(12) United States Patent
Grogan et al.

(10) Patent No.: US 8,137,689 B1
(45) Date of Patent: Mar. 20, 2012

(54) TRANSPLANT/IMPLANT DEVICE AND METHOD FOR ITS PRODUCTION

(75) Inventors: Shawn P. Grogan, Rooty Hill (AU);
Pierre Mainil-Varlet, Bern (CH);
Werner Müller, Wiesendangen (CH);
Thomas Schaffner, Münchenbuchsee (CH)

(73) Assignee: Zimmer GmbH, Winterthur (CH)

( * ) Notice: Subject to any disclaimer, the term of this patent is extended or adjusted under 35 U.S.C. 154(b) by 2188 days.

(21) Appl. No.: 10/129,915

(22) PCT Filed: Nov. 13, 2000

(86) PCT No.: PCT/CH00/00602
§ 371 (c)(1),
(2), (4) Date: Nov. 4, 2002

(87) PCT Pub. No.: WO01/34166
PCT Pub. Date: May 17, 2001

(30) Foreign Application Priority Data

Nov. 11, 1999 (EP) .................................... 99122460

(51) Int. Cl.
*A61F 13/00* (2006.01)
*A61K 9/14* (2006.01)
*A61K 48/00* (2006.01)
*C12N 15/63* (2006.01)
*A01N 43/04* (2006.01)

(52) U.S. Cl. ........ 424/425; 424/484; 424/93.2; 435/455

(58) Field of Classification Search .................. 424/423, 424/424, 425, 426; 523/113, 114
See application file for complete search history.

(56) References Cited

U.S. PATENT DOCUMENTS

| | | | |
|---|---|---|---|
| 4,624,672 A | 11/1986 | Lenkauskas | 623/10 |
| 4,627,853 A | 12/1986 | Campbell et al. | 623/16 |
| 5,206,023 A | 4/1993 | Hunziker | 424/423 |
| 5,368,858 A | 11/1994 | Hunziker | 424/423 |
| 5,741,685 A * | 4/1998 | Vacanti | 435/182 |
| 5,749,874 A | 5/1998 | Schwartz | 606/75 |
| 5,837,235 A | 11/1998 | Mueller et al. | 424/93.7 |
| 5,842,477 A | 12/1998 | Naughton et al. | 128/898 |
| 5,855,610 A * | 1/1999 | Vacanti et al. | 623/2.13 |
| 5,902,741 A * | 5/1999 | Purchio et al. | 435/325 |
| 5,919,702 A | 7/1999 | Purchio et al. | 435/378 |
| 5,965,125 A | 10/1999 | Mineau-Hanschke | 424/93.21 |
| 6,017,348 A | 1/2000 | Hart et al. | 606/79 |
| 6,060,306 A | 5/2000 | Flatt et al. | 435/297.2 |
| 6,143,501 A | 11/2000 | Sittinger et al. | 435/6 |
| 6,179,871 B1 | 1/2001 | Halpern | 623/11.11 |
| 6,235,316 B1 | 5/2001 | Adkisson | 424/548 |
| 6,242,247 B1 * | 6/2001 | Rieser et al. | 435/297.1 |
| 6,251,143 B1 | 6/2001 | Schwartz et al. | 623/23.72 |
| 6,291,240 B1 * | 9/2001 | Mansbridge et al. | 435/395 |
| 6,299,604 B1 * | 10/2001 | Ragheb et al. | 604/265 |
| 6,413,511 B1 | 7/2002 | Glorioso et al. | 424/93.21 |
| 6,451,060 B2 | 9/2002 | Masuda et al. | 623/23.72 |
| 6,849,255 B2 | 2/2005 | Gazit et al. | 424/93.21 |
| 6,852,125 B2 | 2/2005 | Simon et al. | 623/16.11 |
| 6,911,202 B2 | 6/2005 | Amir et al. | 424/93.7 |
| 2001/0010023 A1 | 7/2001 | Schwartz et al. | 623/23.72 |
| 2001/0012965 A1 | 8/2001 | Masuda et al. | 623/11.11 |
| 2001/0039455 A1 | 11/2001 | Simon et al. | 623/23.51 |
| 2002/0072533 A1 | 6/2002 | Schrier et al. | 514/364 |
| 2002/0110544 A1 | 8/2002 | Goldberg et al. | 424/93.7 |
| 2003/0077821 A1 | 4/2003 | Sah et al. | 435/366 |
| 2003/0100947 A1 | 5/2003 | Nadler et al. | 623/11.11 |
| 2003/0134792 A1 | 7/2003 | Pike et al. | 514/12 |
| 2003/0211992 A1 | 11/2003 | Chen et al. | 514/12 |
| 2004/0039447 A1 | 2/2004 | Simon et al. | 623/13.11 |
| 2004/0097405 A1 | 5/2004 | Schrier et al. | 514/2 |
| 2004/0162622 A1 | 8/2004 | Simon et al. | 623/23.5 |
| 2004/0181232 A1 | 9/2004 | Re et al. | 606/86 |
| 2005/0226856 A1 | 10/2005 | Ahlfors | 424/93.7 |

FOREIGN PATENT DOCUMENTS

| | | |
|---|---|---|
| EP | 0 656 767 B1 | 2/2005 |
| EP | 1 112 348 B1 | 11/2005 |
| WO | WO95/33821 A1 | 12/1995 |
| WO | WO97/30662 A1 | 8/1997 |
| WO | WO02/10348 A2 | 2/2002 |
| WO | WO03/024463 A1 | 3/2003 |

OTHER PUBLICATIONS

"Secrete", Stedman's Medical Dictionary, 27th Edition, 2002-2006.*
The term "artificial" is defined as "made by human skill." (Dictionary.com Unabridged, based on the Random House Dictionary, (visited Mar. 15, 2011), HTTP://dictionary.Reference.com/browse/artificial.).*

(Continued)

*Primary Examiner* — Quang Nguyen
(74) *Attorney, Agent, or Firm* — Schwegman, Lundberg & Woessner, P.A.

(57) ABSTRACT

A transplant/implant device for delivering at least one predetermined biologically active compound to a human or animal host system or for another biological function in the host system is produced by genetically engineering vital chondrocytes or mixing chondrocytes with another type of native or genetically engineered cells or mixing chondrocytes with artificial particles having a size comparable to the size of cells or combining at least two of the named steps of engineering or mixing and by subjecting the chondrocytes or the mixture comprising the chondrocytes to three dimensional culture conditions for in vitro production of cartilaginous tissue whereby the cells and/or the artificial particles are immobilized in the cartilaginous tissue. The chondrocytes produce and maintain the cartilaginous tissue and the chondrocytes themselves or cells of another cell type immobilized in the cartilaginous tissue are able to produce and secrete the at least one predetermined compound.

15 Claims, 2 Drawing Sheets

OTHER PUBLICATIONS

The term "artificial" is also defined as "humanly contrived often on a natural model." (Merriam-Webster Online Dictionary, (visited Mar. 15, 2011), HTTP://www.merriam-webster.com/dictionary/artificial.).*

WO 96/34955, "Method of Treating Cartilaginous Diseases With Genetically Modified Chondrocytes", Publication Date: Nov. 7, 1996.

WO/ 97/46665, "Method for Making Cartilage and Implants", Publication Date: Dec. 11, 1997.

Cornell B A et al: "A biosensor that uses ion-channel switches."Nature (London), vol. 387, No. 6633, 1997, pp. 580-583, XP002140886.

Baragi et al: "transplantation of adenovirally transduced allogeneic chondrocytes into articular cartilage defects in vivo", Osteoarthrtis and Cartilage, vol. 5, 1997, pp. 275-282, XP000914934.

Pollok et al: "long-term insulin-secretory function of islets of Langerhans encapsulated with a layer of confluent, chondrocytes for immunoisolation", Pediatr. Surg. Int., vol. 15, 1999, pp. 164-167, XP000914947.

Pollok J-M et al: "Immunoisolation of xenogeneic islets using a living tissue engineered cartilage barrier.", Transplantation Proceedings, vol. 29, No. 4, 1997, pp. 2131-2133, XP000914948.

Aebischer et al., *Brain Res.* 560(1-2):43-49 (1991).

Arai et al., *Journal of Rheumatology* 27(4):979-982 (2000).
Brittberg et al., *N. Engl. J. Med.* 331(14):889-895 (Oct. 6, 1994).
Dharmavaram et al., *Arthritis & Rheum.* 42(7):1433-1442 (Jul. 1999).
Evans et al., *Intern. Med.* 38(3):233-239 (Mar. 1999).
Fan et al., *Diabetes* 39(4):519-522 (Apr. 1990).
Heald et al., *Transplant Proc.* 26(3):1103-1104 (Jun. 1994).
Kandel et al., *Biochim. Biophys. Acta.* 1053(2-3):130-134 (1990).
Kingston, "Introduction of DNA into Mammalian Cells," In: *Current Protocols in Molecular Biology* (Eds. Ausubel, Brent, Kingston, Moore, Seidman, Smith, Struhl), vol. 1, Chapter 9 (1998).
Lechman et al., *J. Immunol.* 163(4):2202-2208 (1999).
Lévesque et al., *Endocrinology* 130(2):644-650 (1992).
Lum et al., *Diabetes* 40(11):1511-1516 (Nov. 1991).
Madry et al., *Gene Therapy* 7(4):286-291 (2000).
Markmann et al., *Transplantation* 49(2):272-277 (Feb. 1990).
Minas et al., *Clin. Sports Med.* 18(1):13-44 (Jan. 1999).
Müller-Ladner et al., *Arthritis & Rheum.* 42(3):490-497 (Mar. 1999).
Selden et al., *Mol. Cell Biol.* 6(9):3173-3179 (Sep. 1986).
Tada et al., *Biochim. Biophys. Acta.* 1201(2):135-142 (1994).
Atkinson et al., *Journal of Cellular Biochemistry* 65:325-339 (1997).
Benz et al., *Biochemical and Biophysical Research Communications* 293:284-292 (2002).
Trippel, *The Journal of Rheumatology* 22:129-132 (1995).

* cited by examiner

TRANSPLANT/IMPLANT DEVICE AND METHOD FOR ITS PRODUCTION

BACKGROUND OF THE INVENTION

1. Field of the Invention

The invention concerns a transplant/implant device according to the generic part of the first independent claim. The device is transplanted in a human or animal host and serves e.g. for in vivo delivery of a predetermined biologically active compound or a plurality of such compounds desired to be present either locally or systemically in the host. The invention also concerns a method according to the corresponding independent claim, the method serving for producing the inventive transplant/implant device.

2. Description of Related Art

For reducing or eliminating conditions caused by hereditary or degenerative malfunction, for treating diseases, for improving healing after injury or surgery, for modifying individual development or growth or for other desired biological functions, hormones, growth factors, activators, inhibitors or other biologically active compounds or factors are administered to humans or animals. It is known how to genetically engineer human or animal cells in order to enable them to produce and secrete such biologically active compounds and it is also known how to administer such compounds to humans or animals by transplantation of vital cells being able or being made able to produce the compounds. The cells to be transplanted in order to deliver the desired compounds within a human or animal host may be native cells (genetically unmodified) usually originating from a suitable donor or they may be genetically engineered cells originating from a donor or from the host himself. Methods for preparing cells being able to produce, secrete, and monitor desired biologically active compounds are described in the following publications:

Using an in vitro retroviral vector delivery system, U Muller-Ladner et al. (Arthritis Rheum 42: 490-497, 1999) reported a successful insertion of interleukin-10 (IL-10) into the genome of human rheumatoid arthritis synovial fibroblasts. ER Lechman et al. (J Immunol 15; 163(4):2202-2208, 1999) reported the direct adenoviral gene transfer of viral IL-10 to rabbit knees with experimental arthritis. The results suggest that direct, local intra-articular delivery of the vIL-10 gene may have polyarticular therapeutic effects.

C H Evans and P D Robbins (Intern Med 38(3):233-239, 1999) also outline several genes encoding anti-arthritic products that can be transferred to intra- or extra-articular sites where their expression suppresses various aspects of the pathophysiology of arthritis. Discussed are two human arthritis gene therapy protocols that are underway in the USA and Germany. Both studies involve the ex vivo transfer of an IL-1 Ra cDNA to the metacarpophalangeal joints of patients with rheumatoid arthritis.

R M Dharmavaram et al. (Arthritis Rheum 42(7):1433-42, 1999) have been able to effect stable transfection of human fetal chondrocytes with a type II procollagen minigene.

R E Kingston outlines many standard protocols of transfecting and transducing mammalian cells (Current Protocols in Molecular Biology, 1: Chapter 9: 9.0.1-9.0.5, 1998).

Transplantation of adenovirally transduced allogeneic chondrocytes into articular cartilage defects in vivo was reported by V M Baragi et al. (Osteoarthritis Cartilage 5(4): 275-282, 1997). These chondrocytes were transduced with a recombinant adenovirus containing the gene for *Escherichia coli* beta-galactosidase (Ad.RSVntlacZ) in order to detect the transduced cells.

The main problems arising when using transplanted vital cells for delivering desired biologically active compounds to a host system or tissue are caused by the difficulty of creating and maintaining (in particular on a long term basis) local conditions in which the transplanted cells are able to survive and to produce and secrete the desired biologically active compounds and from which the compounds can be delivered to the host in a satisfactory manner. This includes prevention or at least reduction of unfavourable reactions by the host, in the case of transplanted heterologous or homologous cells in particular prevention or suppression of immune reactions by the host immune system. For solving these problems and in particular for solving the problem of the immune reaction, varying solutions have been suggested.

According to J F Markmann et al. (Transplantation 49: 272-277,1990) the surface of the cells to be implanted is altered for immune modulation.

According to e.g. P Aebischer et al. (Brain Res: 560(1-2): 43-49, 1991), M Y Fan et al. (Diabetes 39: 519-522,1990), K A Heald et al. (Transplantation P26: 1103-1104, 1994), L Lèvesque et al. (Endocrinology 130: 644-650,1992) or Z-P Lum et al. (Diabetes 40: 1511-1516,1991) the cells to be implanted are encapsulated for immunoisolation. This means that immune suppression is avoided by preventing immune recognition and rejection through separating the transplanted cells from the host immune system with the aid of artificial barrier materials such as, for example, semipermeable membranes, hollow fiber devices, hydrogels, alginate capsules, a polyanionic colloid matrix, etc. However, not all these materials are completely inert and they can induce a foreign-body and/or inflammatory reaction resulting in fibrous tissue overgrowth, which may diminish the diffusion properties of the devices.

J P Vacanti (U.S. Pat. No. 5,741,685) and J-M Pollok et al. (Pediatr Surg Int 15: 164-167, 1999) describe the use of a tissue-engineered capsule of chondrocytes for the immunoisolation of islets of Langerhan cells. Islet cells are collected and immobilized within a polymer matrix. Concomitantly, chondrocytes are cultured in monolayers to proliferation. The confluent sheet of expanded chondrocytes is then used to wrap around the polymer matrix containing the islet cells. According to Pollok, islets taken from rats were encapsulated in a membrane containing bovine chondrocytes and their behaviour was observed in vitro for 30 days. No immune reaction of the bovine tissue against the rat cells was observed and the chondrocytes were still vital after the 30 days. The device comprising the islets encapsulated in the matrix were still secreting insulin after the 30 days, however on a reduced scale compared with the time immediately after encapsulation.

The immunoisolation method according to Vacanti and Pollok et al. is based on the knowledge of the immunoprivileged properties of the chondrocyte matrix and uses these properties for creating an immunoisolating barrier between allogic or xenogenic islets and the host immune system.

SUMMARY OF THE INVENTION

It is an object of the invention to create a transplant/implant device suitable for transplantation or implantation in a human or animal host and serving for delivery of at least one predetermined biologically active compound and/or for at least one other biological function. The device is to be able to maintain the desired function over a predetermined term in particular over a long term after transplantation by creating and maintaining suitable conditions for cells or artificial particles which are contained in the device and which are responsible for the desired function and by preventing or reducing unfavourable reactions of the host system e.g. reactions by the host immune system or unfavourable foreign-body reactions of the host tissue in which the device is implanted.

It is a further object of the invention to create a method for producing the inventive transplant device.

The inventive device comprises vital cartilaginous tissue that is produced and maintained by chondrocytes. It further comprises vital cells or artificial particles of a size comparable to the size of cells which cells or particles are responsible for the desired function (e.g. delivery of a biologically active compound). The cells or particles are immobilized within the matrix of the cartilaginous tissue. The cells being able to produce and secrete a predetermined biologically active compound are preferably the chondrocytes being suitably engineered, which chondrocytes at the same time are responsible for producing and maintaining the extracellular matrix of the device.

The vital cartilaginous tissue not only proves privileged regarding immuno reaction but also proves well suited for maintaining cells able to carry out a predetermined function, for delivering compounds produced and secreted by these cells to the host system and for preventing foreign-body, inflammatory or abnormal growth reactions of the host tissue known from implantations of artificial materials.

Other than in the devices according to Vacanti and Pollok et al. (see above), the chondrocytes of the inventive device not only serve for shielding implanted cells from host reactions but also produce and maintain a suitable matrix for immobilizing the transplanted cells or artificial materials and provide immediate surroundings favouring their vitality and functionality.

BRIEF DESCRIPTION OF THE DRAWINGS

The following Figures illustrate the Example at the end of the present specification and illustrate the ability of suitably transfected chondrocytes to secrete human growth hormone (hGH) during in vitro culture.

DETAILED DESCRIPTION OF THE PREFERRED EMBODIMENTS

Figure 1:
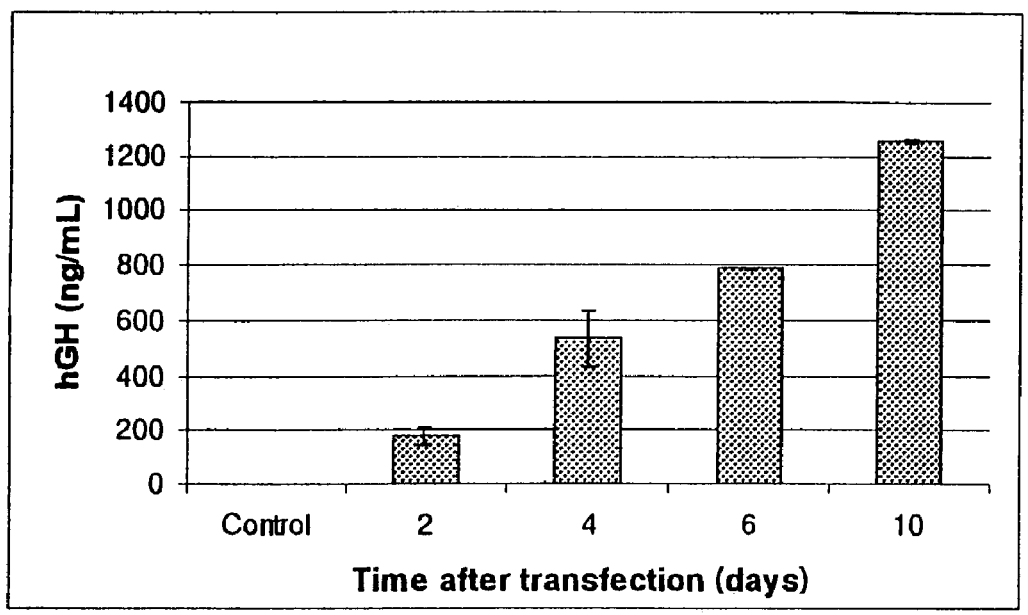
FIG. 1 shows the cumulative human growth hormone conc. (ng/mL) of media from monolayer cultured rat chondrocytes transfected with pXGH5 plasmid.

The term chondrocytes is used in the present specification to denominate cells being able to produce and maintain an extracellular matrix having the main characteristics of native cartilage (containing type II collagen and proteoglycanes). The cells originate from cartilaginous tissue or they are prepared by in vitro differentiation of stem cells.

The term cartilaginous tissue is used in the present specification to denominate a tissue comprising vital chondrocytes and an extracellular matrix produced and maintained by the vital chondrocytes. The cartilaginous tissue of the inventive device is produced in vitro starting from vital chondrocytes using, for example, the method according to the European patent No. 0922093, the disclosure of which is incorporated herein by reference in its entirety, or any other 3D culture system.

The vital chondrocytes of the cartilaginous tissue of the inventive device are autologous, homologous or heterologous. They are embedded in the extracellular cartilaginous matrix of the device, which matrix is produced and maintained by these chondrocytes. Immobilized within the extracellular matrix, the inventive device comprises genetically engineered or native cells and/or artificial particles responsible for the desired function. These immobilized cells may also be autologous, homologous or heterologous and may serve, for example, for producing and secreting at least one predetermined biologically active compound. The artificial particles may, for example, be biosensors in the form of nanomachines and may serve, for example, for monitoring a predetermined metabolic activity.

In a preferred embodiment of the inventive device, the chondrocytes producing and maintaining the cartilaginous tissue themselves or at least a part of them are genetically engineered such that they are able not only to produce and maintain the cartilaginous tissue but also made able to produce and secrete at least one predetermined biologically active compound by suitable genetical engineering.

In addition to its known immune privileged properties, the cartilaginous matrix being maintained before and after implantation by the vital chondrocytes proves to have optimal characteristics for sustaining on a long term basis the vitality and productive capability of cells able to produce and secrete desired compounds and for delivering the compounds to the host system or tissue. One reason for this may be the fact that chondrocytes in e.g. articular cartilage live significantly longer compared to other cell types, that they require limited nutrient supply and that they are able to naturally maintain the cartilaginous matrix.

The inventive method for producing an inventive transplant/implant device comprises the steps of:
 providing a suitable number of vital chondrocytes:
 genetically engineering at least part of the chondrocytes or mixing the chondrocytes with another type of native or genetically engineered cells or mixing the chondrocytes with artificial particles having a size comparable to the size of cells or combining at least two of the named steps of engineering or mixing;
 subjecting the chondrocytes or the mixture comprising the chondrocytes to three dimensional culture conditions for in vitro production of cartilaginous tissue.

The device produced in the above three method steps is then transplanted or implanted into the host.

As source of the chondrocytes, articular, rib, nasal, or ear cartilage may be harvested from a donor or from the host or the cells may be derived from eye lenses of foetal or adult human or animal origin or from an intervertebral disk with its annulus pulpusus.

The chondrocytes and further native or genetically engineered cells of another cell type used for producing the mixture of cells may originate both from the host or from a donor or may originate from different individuals.

An example of artificial particles being mixed with the chondrocytes are biosensors in the form of nanomachines as described e.g. by B A Cornell et al. (Nature 1997 Jun. 5; 387(6633): 555-557).

Depending on the size of transplant needed, a step of proliferating the chondrocytes in vitro (monolayer culture) may be required (before and/or after the step of genetically engineering the chondrocytes).

In particular for an inventive device comprising homologous or heterologous cells it is advantageous to remove cells near the surface of the in vitro cultivated cartilaginous tissue.

An autotransplant device according to the invention and serving as a delivery device for interleukins is, for example, produced with the following method steps:

- harvesting cartilaginous tissue from the human or animal host (e.g. by cartilage biopsy), preparing the chondrocytes of the tissue according to standard primary culture preparation methods and expanding the chondrocytes in a monolayer culture;
- genetically engineering the chondrocytes in the monolayer for enabling them to produce and secrete interleukins (e.g. according to the method described in the publication mentioned above by Muller-Ladner, 1999, Lechman et al. 1999 or Evans and Robbins, 1999);
- cultivating the engineered chondrocytes in vitro for producing a three dimensional cartilaginous matrix (e.g. according to EP-0922093) and screening the construct for the amount of interleukin produced.

Examples of standard methods to collect and process cartilage from slaughterhouse animals are described by Pollok et al. 1999. To harvest cartilage via biopsies (human) see e.g. M Brittberg et al. (New England Journal of Medicine 331(14): 889-895,1994) and T Minas and L Peterson (Clin Sports Med 18(1):13-44 v-vi, 1999). Examples of standard preparation of primary cultures from intact cartilage are described e.g. by Kandel et al. (Biochim. Biophys. Acta. 1035:130, 1990) and by Pollok et al., 1999. Standard cell culture systems and equipment are used for the step of monolayer expansion.

According to U.S. Pat. No. 5,919,702 pre-chondrocytes isolated from umbilical cord, in particular from Wharton's jelly are a further source for the chondrocytes used in the inventive method.

An assortment of methods of introducing gene products into cells and monitoring transfer efficiencies are described in Kingston (1998).

Methods of three-dimensional culture for formation of an inventive device are described in the European patent No. 0922093. Standard kits (e.g. ELISA) and protocols supplied by many manufactures are used to measure delivery of a predetermined product (e.g. interleukins) in in vitro conditions prior to implanting the device.

The inventive device is applicable for local administration of biologically active compounds, for example, implanted within a joint and delivering morphogenic factors or growth factors for recovery of a cartilage defect or interleukins to inhibit inflammation. Or it is applicable for systemic administration, for example, implanted in a blood vessel or abdominal cavity and delivering somatotropin and insulin. The inventive device is applicable for permanent delivery, i.e. for delivery during a very long time, or it can be removed after a limited delivery period.

Further examples of applications of the inventive device are:

- supplementing hormones (or correcting hormone levels) like insulin for diabetes or parathyroid hormone in hypocalcemia;
- augmenting growth of livestock by administration of somatotropin;
- augmenting wound healing via release of maturation and growth factors like BMP for treatment of pseudoarthrosis;
- supplying absent hormone or factor like coagulation factors in haemophilia or dopamine in Parkinson's disease;
- supplying therapeutic agents such as ciliary neurotrophic factor (CNTF) for the treatment of human neurodegenerative diseases such as amyotrophic lateral sclerosis (ALS);
- supplying activators or inhibitors of angiogenesis for tumour treatment and wound healing;
- provide a live substrate for biosensors measuring metabolic activities and controlling hormone release.

The main advantages of the inventive transplant device and of the method for producing it are the following:

The cells that produce and maintain the matrix may be of the same type (chondrocytes) as the ones producing the predetermined product.

The matrix of the device has inherit stabilisation qualities suitable for implantation procedures.

The used culture technique to produce the transplant is technically less demanding compared to techniques involving artificial barrier encapsulation methods.

The culture technique using co-cultures of chondrocytes and other cells is technically less demanding compared to the protocol described e.g. by Pollock et al. (1999).

The inventive device is longer lasting than known gene-transfer models which are limited by the problem of decreasing expression of the transfected gene over time, and the inventive device can be removed when required.

EXAMPLE

Chondrocytes originating from rat articular cartilage were suitably transfected to be able to secrete human growth hormone (hGH). The chondrocytes were then cultured in pellets. Human growth hormone concentrations in the culture media were monitored. As it is known that Dexamethasone can induce an increased production of hGH, due to the existence of glucocorticoid enhancer sequences in the pXGH5 plasmid (Selden et al. 1986), Dexamethasone was tested as molecular switch.

Tissue collection and culture techniques: Cartilage was obtained aseptically from the articular knee joint of a 12 month old Wistar Rat and subsequently digested in 2.5 mg/10 mL Collagenase P (Roche) in HAM-F12 (Gibco BRL) with 5% FBS (HyClone), insulin (250 µg/mL; Gibco BRL) and vitamin C (12.5 µg/mL; Fluka) at 37° C. in a shaking water bath for 12 hours. The digested slurry was pipetted through a cell strainer (100 µm; Falcon), washed in PBS (pH 7.4) and counted. Cells were seeded at a density of 930,000 cells per $cm^2$ in T25 flasks (Falcon) and allowed to expand at 37° C. in 4 mL HAM-F12 supplemented with 10% FBS, insulin, Vitamin C, penicillin (100,000 IE/mL; Sigma), streptomycin (10,000 µg/mL; Sigma) and Amphotericin B (250 µg/mL; Sigma). Cells were allowed to expand until 80-90% confluence and then were exposed to 1xEDTA/Trypsin (Gibco BRL) and subsequently passaged 3 times.

Transfections: The plasmid pXGH5 with the human growth hormone (hGH) insert was used in the transfections (See Selden et al. 1986). The plasmid was amplified in *E. coli* HB101 (Promega) and subsequently purified using a plasmid extraction kit (Qiagen). One day before transfections, the chondrocytes were re-seeded at a density between 50 and 80% confluence in HAM-F12 with 10% FBS, but without other additives. The following day, FuGENE 6 (Roche) and the purified plasmid DNA (1 µg) was added to 100 µL of HAM-F12 without other additives as detailed in the manufacturer's manual. This mixture was added to the assigned T25 flasks containing the rat chondrocytes. Mock transfections with only FuGENE 6 were also made. Samples of 200 μL was obtained from the media of the transfected and control untransfected cells in monolayer at various time intervals following transfection. These samples were stored at −20° C. until assessed for hGH concentrations using an ELISA assay kit (Roche), which does not cross-react with rat GH.

Three dimensional cultures: Transfected cells were detached from confluent flasks as outlined previously, counted and allocated into 1.5 mL eppendorf tubes at a density of $6.3 \times 10^5$ cells. These tubes were then centrifuged at 1000 g for 5 minutes to form a pellet. All tubes were incubated in standard culture conditions and the media was also sampled over time to assess changes in hGH levels.

Dexamethasone treatment: Both monolayer and 3-D pellet cultures ($5.2 \times 10^5$ cells per pellet) were exposed to Dexamethasone (Dex, Sigma) at concentrations of 0.1 μM, 0.01 μM and 0.001 μM for 24 hours to study the effect of Dex on hGH release.

Figure 2:
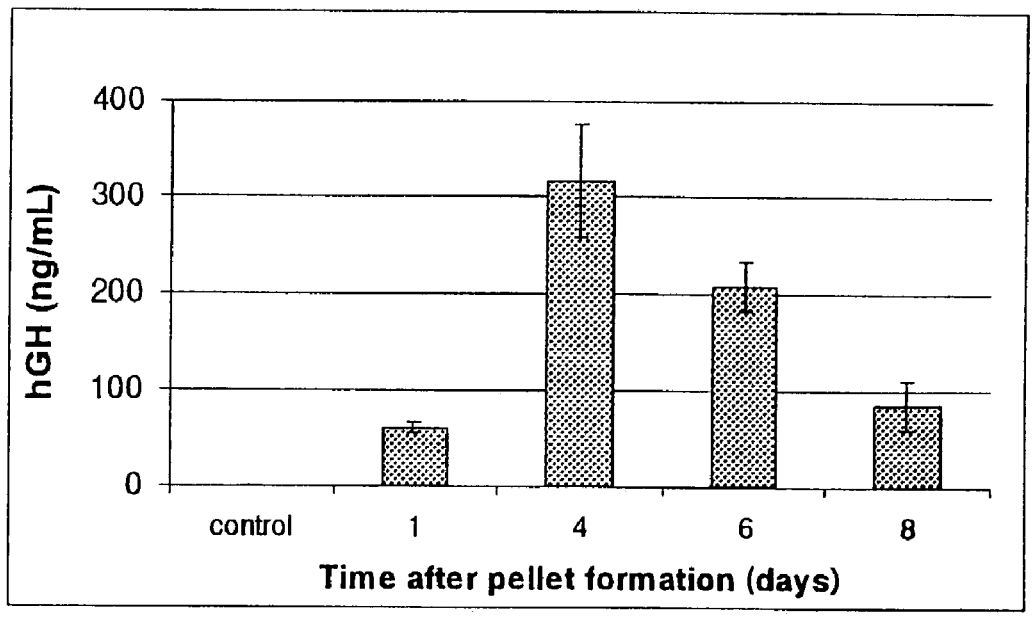
FIG. 2 shows the human growth hormone conc. (ng/mL) of media from pellet cultured rat chondrocytes transfected with pXGH5 plasmid following pellet formation.
Figure 3:
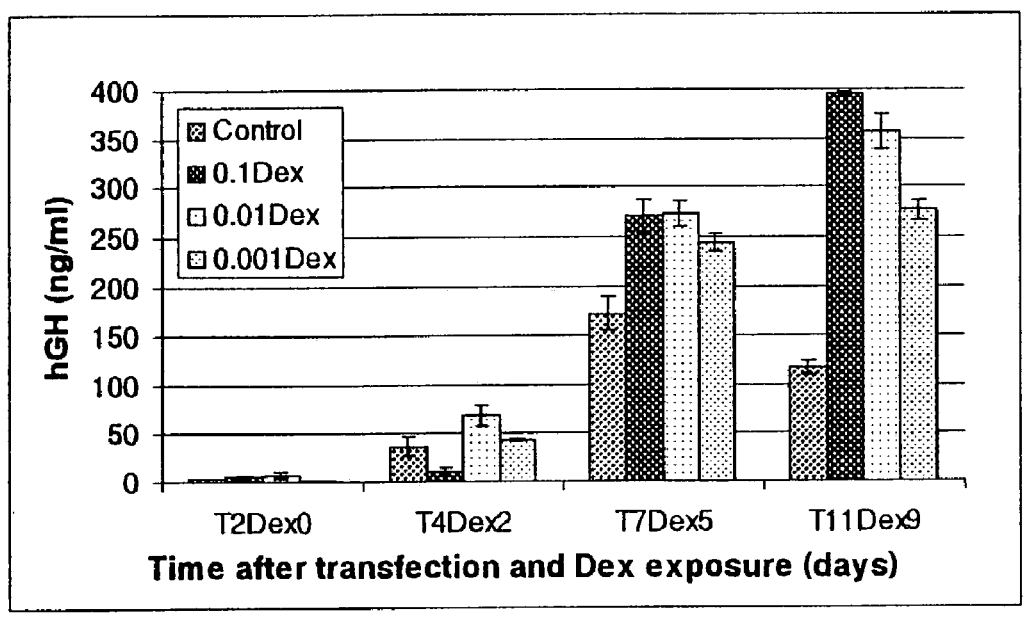
FIG. 3 shows the cumulative human growth hormone concentrations (ng/mL) of media from monolayer cultured rat chondrocytes transfected with pXGH5 at different times following transfection and Dex treatment.
Figure 4:
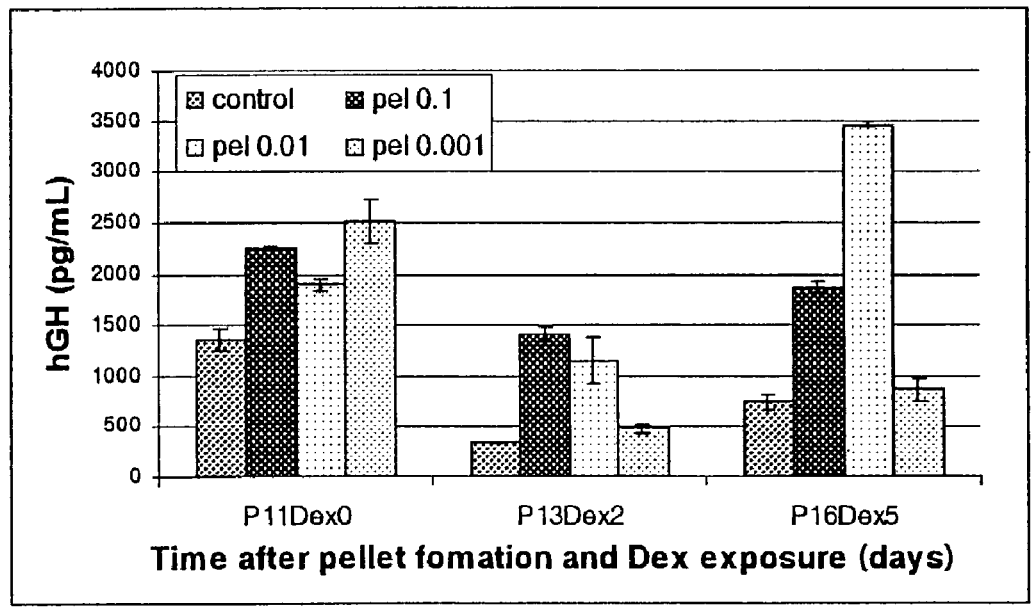
FIG. 4 shows the human growth hormone concentrations (pg/mL) of media from pellet cultured rat chondrocytes ($5.2 \times 10^5$ cells per pellet) transfected with pXGH5 at different times following pellet formation and Dex treatment.

Results: Rat chondrocytes transfected with pXGH5 produced hGH to levels of 200 ng/mL by 2 days and accumulated to 1200 ng/mL by day 10 (FIG. 1). Transfected rat chondrocytes in pellet culture ($6.3 \times 10^5$ cells/pellet) also released hGH into the culture medium, peaking between day 1 and 4 to about 300 ng/mL. A reduction was noted thereafter, to levels close to 100 ng/mL by day 8 of pellet culture (FIG. 2). The addition of Dex to monolayer chondrocytes, at all concentrations tested, increased the production of hGH (FIG. 3, T=days after transfection Dex=days after Dex exposure: (0.1 μM, 0.01 μM and 0.001 μM). Further, Dex at concentrations of 0.1 μM and 0.01 μM maintained a higher hGH concentration in the medium of pellet cultured transfected rat chondrocytes compared to controls (FIG. 4, P=days after pellet formation; Dex=days after Dex exposure: (0.1 μM, 0.01 μM and 0.001 μM).

REFERENCES

Aebischer P; Tresco P A; Sagen J; Winn S R. 1991. Transplantation of microencapsulated bovine chromaffin cells reduces lesion-induced rotational asymmetry in rats. Brain Res. 560(1-2):43-49.

Arai Y; Kubo T; Fushiki S; Mazda O; Nakai H; Iwaki Y; Imanishi J; and Hirasawa Y. 2000. Gene delivery to human chondrocytes by an adeno associated virus vector. Journal of Rheumatology. 27(4):979-982.

Baragi V M; Renkiewicz R R; Qiu L; Brammer D; Riley J M; Sigler R E; Frenkel S R; Amin A; Abramson S B; Roessler B J. 1997. Transplantation of adenovirally transduced allogeneic chondrocytes into articular cartilage defects in vivo. Osteoarthritis Cartilage. 5(4):275-282.

Brittberg M; Lindahl A; Nilsson A; Ohisson C; Isaksson O; Peterson L. 1994. Treatment of deep cartilage defects in the knee with autologous chondrocyte transplantation. N Engl J Med. 331(14):889-895.

Cornell B A; Braach-Maksvytis V L; King L G; Osman P D; Raguse B; Wieczorek L; Pace R J. 1997. A biosensor that uses ion-channel switches. Nature. 387(6633):580-583.

Dharmavaram R M; Liu G; Tuan R S; Stokes D G; Jimenez S A. 1999. Stable transfection of human fetal chondrocytes with a type II procollagen minigene: expression of the mutant protein and alterations in the structure of the extracellular matrix in vitro. Arthritis Rheum. 42(7):1433-1442.

Evans C H; Robbins P D. 1999. Gene therapy of arthritis. Intern Med. 38(3):233-239.

Fan M Y; Lum Z P; Fu X W; Levesque L; Tai I T; Sun A M. 1991. Reversal of diabetes in BB rats by transplantation of encapsulated pancreatic islets. Diabetes. 39(4):519-522.

Heald K A; Jay T R; Downing R. 1994. Prevention of antibody-mediated lysis of islets of Langerhans by alginate encapsulation: effect of capsule composition. Transplant Proc. 26(3):1103-1104.

Kandel R A; Pritzker K P; Mills G B; Cruz T F. 1990. Fetal bovine serum inhibits chondrocyte collagenase production: interleukin 1 reverses this effect. Biochim Biophys Acta. 1053(2-3): 130-134.

Kingston R. E. 1998. Introduction of DNA into mammalian cells. In: Current protocols in molecular biology. (Eds. Frederick M Ausubel; Roger Brent, Robert E. Kingston; David D. Moore, J. G. Seidman; John A. Smith and Kevin Struhl). Volume 1. Chapter 9.

Lechman E R; Jaffurs D; Ghivizzani S C; Gambotto A; Kovesdi I; Mi Z; Evans C H; Robbins P D. 1999. Direct adenoviral gene transfer of viral IL-10 to rabbit knees with experimental arthritis ameliorates disease both injected and contralateral control knees. J. Immunol. 163(4):2202-2208.

Lèvesque L; Brubaker P L; Sun A M. 1992. Maintenance of long-term secretory function by microencapsulated islets of Langerhans. Endocrinology. 130(2):644-650.

Lum Z P; Tai I T; Krestow M; Norton J; Vacek I; Sun A M. 1991. Prolonged reversal of diabetic state in NOD mice by xenografts of microencapsulated rat islets. Diabetes. 40(11):1511-1516.

Madry H; and Trippel S B. 2000. Efficient lipid-mediated gene transfer to articular chondrocytes. Gene Therapy. 7(4):286-291.

Markmann J F; Tomaszewski J; Posselt A M; Levy M M; Woehrle M; Barker C F; Naji A. 1990. The effect of islet cell culture in vitro at 24 degrees C. on graft survival and MHC antigen expression. Transplantation 49(2):272-277.

Minas T; Peterson L. 1999. Advanced techniques in autologous chondrocyte transplantation. Clin Sports Med. 18(1): 13-44, v-vi.

Muller-Ladner U; Evans C H; Franklin B N; Roberts C R; Gay R E; Robbins P D; Gay S. 1999. Gene transfer of cytokine inhibitors into human synovial fibroblasts in the SCID mouse model. Arthritis Rheum. 42(3):490-497.

Pollok J M; Ibarra C; Broelsch C E; and Vacanti J P. 1998. Immunisolation xenogener Langerhansscher Inseln in einer mittels Tissue Engineering geformten autologen Knorpel-Kapsel. Zentralbl Chir. 123(7):830-833.

Pollok J M; Begemann J F; Kaufmann P M; Kluth D; Broelsch C E; Izbicki J R; Rogiers X. 1999. Long-term insulin-secretory function of islets of Langerhans encapsulated with a layer of confluent chondrocytes for immunoisolation. Pediatr. Surg. Int. 15(3-4):164-167.

Selden, R. F.; Howie, K. B.; Rowe, M. E.; Goodman, H. M.; and Moore, D. D. 1986. Human growth hormone as a reporter gene in regulation studies employing transient gene expression. Mol Cell Biol. 6(9):3173-3179.

Tada K; Fukunaga T; Wakabayashi Y; Masumi S; Sato Y; Izumi H; Kohno K; and Kuwano M. 1994. Inhibition of tubular morphogenesis in human microvascular endothelial cells by co-culture with chondrocytes and involvement of transforming growth factor beta: a model for avascularity in human cartilage. Biochim Biophys Acta. 1201(2): 135-142.

Vacanti, J. P. 1998. U.S. Pat. No. 5,741,685.

The invention claimed is:

1. An implant for in vivo production of at least one predetermined biologically active compound, said implant comprising chondrocytes producing and maintaining an extracellular matrix and artificial particles producing the at least one predetermined compound, wherein at least some of the artificial particles are disposed within the extracellular matrix and other than the artificial particles, the implant is generated in vitro without the use of a three dimensional artificial matrix.

2. The implant according to claim 1, wherein the chondrocytes comprise autologous chondrocytes originating from a human or animal into which the implant is to be implanted.

3. The implant according to claim 1, wherein the chondrocytes are heterologous or homologous chondrocytes.

4. The implant according to claim 1, further comprising genetically engineered cells.

5. The implant according to claim 4, wherein the genetically engineered cells are chondrocytes.

6. The implant according to claim 1, wherein the compound is selected from the group consisting of inhibitors of inflammation, hormones, growth factors, coagulation factors, neurotransmitters, neurotrophic factors, and activators or inhibitors of angiogenesis.

7. The implant according to claim 1, wherein the particles are of a size comparable to the size of the cells.

8. The implant of claim 1, wherein the extracellular matrix comprises type II collagen and proteoglycans.

9. The implant of claim 1, wherein the chondrocytes originate from cartilaginous tissue.

10. The implant of claim 1, wherein the chondrocytes are prepared by in vitro differentiation of stem cells or pre-chondrocytes.

11. The implant of claim 1, wherein at least some of the artificial particles disposed within the extracellular matrix are immobilized within the extracellular matrix.

12. The implant of claim 6, wherein the compound is a hormone selected from the group consisting of insulin, parathyroid hormone, and somatotropin.

13. The implant of claim 12, wherein the hormone is insulin.

14. The implant of claim 6, wherein the compound is a growth factor.

15. The implant of claim 14, wherein the growth factor is a bone morphogenic protein.

* * * * *